United States Patent
Touya et al.

(10) Patent No.: US 9,406,117 B2
(45) Date of Patent: Aug. 2, 2016

(54) INSPECTION SYSTEM AND METHOD FOR INSPECTING LINE WIDTH AND/OR POSITIONAL ERRORS OF A PATTERN

(71) Applicant: NuFlare Technology, Inc., Yokohama (JP)

(72) Inventors: Takanao Touya, Kanagawa (JP); Shuichi Tamamushi, Kanagawa (JP); Hidenori Sato, Kanagawa (JP); Hiroyuki Tanizaki, Mie (JP); Takeshi Fujiwara, Kanagawa (JP); Eiji Sawa, Kanagawa (JP); Kentaro Okuda, Kanagawa (JP); Hiroyuki Ikeda, Kanagawa (JP); Hiromu Inoue, Kanagawa (JP); Hiroshi Tsukada, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 0 days.

(21) Appl. No.: 14/665,880

(22) Filed: Mar. 23, 2015

(65) Prior Publication Data
US 2015/0193918 A1    Jul. 9, 2015

Related U.S. Application Data

(62) Division of application No. 13/083,157, filed on Apr. 8, 2011, now Pat. No. 9,036,896.

(30) Foreign Application Priority Data

Apr. 9, 2010    (JP) .................................. 2010-090057

(51) Int. Cl.
*G06K 9/00* (2006.01)
*G06T 7/00* (2006.01)
(Continued)

(52) U.S. Cl.
CPC ............ *G06T 7/001* (2013.01); *G01N 21/9501* (2013.01); *G01N 21/9503* (2013.01);
(Continued)

(58) Field of Classification Search
USPC .......... 382/141, 144–152, 209, 216–218, 291
See application file for complete search history.

(56) References Cited

U.S. PATENT DOCUMENTS 4,783,826 A * 11/1988 Koso ............................ 382/147
6,324,298 B1 * 11/2001 O'Dell et al. ................. 382/149
(Continued)

FOREIGN PATENT DOCUMENTS

JP    54-72076    6/1979
JP    7-260699    10/1995
(Continued)

OTHER PUBLICATIONS

Heebom Kim, et al., "IntenCD™: an application for CD Uniformity mapping of photomask and process control at maskshops", Proc. of SPIE, vol. 7028, 70281K, 2008, pp. 1-6.
(Continued)

*Primary Examiner* — Eric Rush
(74) *Attorney, Agent, or Firm* — Oblon, McClelland, Maier & Neustadt, L.L.P.

(57) ABSTRACT

A method and system for imaging an object to be inspected and obtaining an optical image; creating a reference image from design pattern data; preparing an inspection recipe including one or more templates and parameter settings necessary for the inspection; checking the pattern and the template against each other, and selecting the reference image which corresponds to the template; detecting first and second edges in the selected reference image in accordance with the parameter setting using determined coordinates as a reference; detecting first and second edges in the optical image, this optical image corresponds to the selected reference image; and determining an inspection value by acquiring the difference between the line width of the optical image and the reference image using the first edge and second edge of the reference image and the first and second edges of the optical image.

6 Claims, 12 Drawing Sheets

(51) Int. Cl.
*G01N 21/95* (2006.01)
*G01N 21/956* (2006.01)

(52) U.S. Cl.
CPC ............. *G01N21/956* (2013.01); *G06T 7/004* (2013.01); *G06T 7/0004* (2013.01); *G06T 7/0006* (2013.01); *G06T 7/0044* (2013.01); *G06T 7/0085* (2013.01); *G06T 2207/10004* (2013.01); *G06T 2207/30141* (2013.01); *G06T 2207/30148* (2013.01)

(56) References Cited

U.S. PATENT DOCUMENTS

| | | | |
|---|---|---|---|
| 7,133,549 | B2 | 11/2006 | Eran et al. |
| 7,466,854 | B2 | 12/2008 | Sawa et al. |
| 2004/0146194 | A1* | 7/2004 | Ichikawa et al. ............... 382/145 |
| 2005/0146714 | A1* | 7/2005 | Kitamura et al. ........... 356/237.2 |
| 2006/0280358 | A1* | 12/2006 | Ishikawa ................ G06T 7/001 382/149 |
| 2007/0053578 | A1* | 3/2007 | Harabe ......................... 382/145 |
| 2007/0172111 | A1* | 7/2007 | Ikeda ............................ 382/149 |
| 2010/0074511 | A1* | 3/2010 | Tamamushi ..... G01N 21/95607 382/141 |

FOREIGN PATENT DOCUMENTS

| | | |
|---|---|---|
| JP | 2003-43663 | 2/2003 |
| JP | 2003-57009 | 2/2003 |
| JP | 2003-279319 | 10/2003 |
| JP | 2005-277395 | 10/2005 |
| JP | 2007-72173 | 3/2007 |
| JP | 2008-83652 | 4/2008 |
| JP | 2008-112178 | 5/2008 |
| JP | 2009-294123 | 12/2009 |

OTHER PUBLICATIONS

Office Action issued Mar. 27, 2012, in Japanese Patent Application No. 2010-090057 (with English-language translation).

Office Action issued Sep. 14, 2012 in Korean Application No. 10-2011-32731 (With English Translation).

Notification of Reasons for Refusal issued Nov. 27, 2012 in Japanese Patent Application No. 2010-090057 (with English translation).

Combined Taiwanese Office Action and Search Report issued Sep. 25, 2013 in Patent Application No. 100112290 (with English language translation).

* cited by examiner

Fig. 6

| | Name of Item | Value | Explanation |
|---|---|---|---|
| First Edge Retrieval Information | Mask ID | 9653-AA | Mask ID including assignment of layer |
| | Template | 1 | Assignment of Matching Template |
| | Start of Search X Coordinate | -23.4 | Relative Position to Matching Standard Coordinates |
| | Start of Search Y-Coordinate | -23.4 | |
| | End of Search X Coordinate | 0 | Relative Position to Matching Standard Coordinates or Relative Position to search Start Coordinates |
| | End of Search Y-Coordinate | 23.4 | |
| | Measurement of Width | 0 | Measurement Width (nm - Nanometer) (if width is 0, it is measured at only one point) |
| | Threshold of Measurement | 100 | Threshold level of CD (Critical Dimension) measurement |
| | Black and White Color assignment | 1 | 0 : No limit, 1 : white, 2 : black |
| | Assignment of Completed Coordinates | 1 | 0 : Standard of Matching Standard Coordinates 1 : Standard of search Start Coordinates |
| Second Edge Retrieval Information | Mask ID | 9653-AA | Mask ID including assignment of layer |
| | Template | 1 | Assignment of Matching Template |
| | Start of Search X Coordinate | -23.4 | Relative Position to Matching Standard Coordinates |
| | Start of Search Y-Coordinate | 23.4 | |
| | End of Search X Coordinate | 0 | Relative Position to Matching Standard Coordinates or Relative Position to search Start Coordinates |
| | End of Search Y-Coordinate | -23.4 | |
| | Measurement of Width | 0 | Measurement Width (nm - Nanometer) (if width is 0, it is measured at only one point) |
| | Threshold of Measurement | 100 | Threshold level of CD (Critical Dimension) measurement |
| | Black and White Color assignment | 1 | 0 : No limit, 1 : white, 2 : black |
| | Assignment of Completed Coordinates | 1 | 0 : Standard of Matching Standard Coordinates 1 : Standard of search Start Coordinates |
| Control Value of CD (standard) | | 15 | Control value of CD (standard) (nm - Nanometer) |
| Control Value of Dimensional Error (standard) | | 8 | Control Value of Dimensional Error (standard) (nm - nanometer) |
| Object of Measurement | | 0 | Difference of Reference Image and Optical Sensor Image 1 : Absolute Value of Sensor |

INSPECTION SYSTEM AND METHOD FOR INSPECTING LINE WIDTH AND/OR POSITIONAL ERRORS OF A PATTERN

CROSS-REFERENCE TO RELATED APPLICATION

This application is a divisional of U.S. application Ser. No. 13/083,157, filed Apr. 8, 2011, which claims priority to Japanese patent application No. 2010-090057, filed Apr. 9, 2010. The entire contents of these applications are incorporated herein by reference.

BACKGROUND OF THE INVENTION

1. Field of the Invention

The present invention relates to an inspection method and an inspection system for inspecting a line width or a positional of a pattern formed on an object to be inspected, such as a mask.

2. Background Art

Recently, the line width of circuits required for semiconductor devices has become increasingly narrower due to further integration and increases in capacity of large-scale integrated circuits (LSI). Semiconductor devices are manufactured via circuit formation by exposure transfer of a pattern on a wafer with a reduced projection exposure device called a "stepper", using an original image pattern with a circuit pattern formed thereon, these are called masks or reticles (hereinafter referred to collectively as masks). Masks used to transfer such fine circuit patterns to the wafer are manufactured by electron beam writing apparatuses, which can write micropatterns. Further, the development of a laser beam lithography device, which can write using a laser beam is also being attempted. An electron beam lithography device is also used when directly writing a circuit pattern onto a wafer.

Since the cost of manufacturing LSIs is very high, an increase in yield is required to make the manufacturing economically feasible. Meanwhile, in recent representative logic devices, formation of a pattern with a line width of several-ten nanometers (nm) is now required. Pattern defects in the mask and fluctuations in the process conditions during exposure transfer may be large factors in the reduction of yield. Further, major factors that reduce the yield include a mask containing a pattern defect and a variation in conditions of the exposure transfer. As a result, in the mask inspection process, dimensions which must now be detected as pattern defects are miniaturized, and it becomes necessary to detect extremely small positional errors of the pattern. Thus, high accuracy is required for inspection systems to inspect the dimensions of masks used in LSI manufacture.

As a method for detecting pattern defects, mention may be made of a die-to-die inspection system and a die to database inspection system. The die-to-die inspection system is used when the mask to be inspected has thereon a plurality of identical chip patterns, or a plurality of chip patterns each including an identical pattern segment. According to this system, since mask patterns are directly compared, a highly accurate inspection can be carried out with a relatively simple device configuration. However, defects, which are common to both patterns being compared cannot be detected. On the other hand, in the die-to-database inspection method, an actual pattern on a mask is compared to reference data generated from the design pattern data that was used to manufacture the mask. Thus, this method allows exact comparison of the pattern with the design pattern data, although the required system size is large since the method requires a processing system for generating a reference image. There is no choice but to use this inspection method when the mask to be inspected has only one chip pattern to be transferred to the wafer.

In die-to-die inspection, light is emitted from a light source, and the mask to be inspected is irradiated with this light through an optical system. The mask is mounted on a table, and this table is moved so that the emitted beam of light scans the surface of the mask. Light transmitted through, or reflected from the mask, reaches an image sensor via a lens, thereby forming an image thereon. The optical image thus formed on the image sensor is sent to a comparing unit as measurement data. The comparing unit compares the measurement data with reference data in accordance with an appropriate algorithm, and if they are not identical, the mask is determined to have a defect (See Japanese Patent Application Laid-Open (JP-A) No. 2008-112178)

In a conventional inspection system, a mask pattern image, obtained by imaging an optical image with an optical image sensor is determined to be correct. However, with the recent miniaturization of a device pattern on a mask, it is difficult to distinguish the difference between an unwanted pattern defect and the correct pattern. Furthermore, if positional defects or a line width difference of the pattern are measured using this method, a problem arises in that the measured value fluctuates depending on the pattern. This means that the positional defects or the line width difference across the entire surface of the mask cannot be accurately calculated. This kind of problem is prominent in a logic mask which has many patterns, and thus the development of a method which can measure accurately each pattern is necessary. The need to accurately control the dimensions of patterns has thus increased the difficulty of manufacturing masks. As a result, there has been a loss in the yield of masks that meet the required specifications, thereby raising the cost of mask manufacturing.

The present invention was created in consideration of the above circumstances, and an object of the present invention is to provide an inspection method and an inspection system that can accurately calculate the distribution of line width difference or the distribution of positional aberration of a pattern formed on a mask and a reference pattern.

Other challenges and advantages of the present invention are apparent from the following description.

SUMMARY OF THE INVENTION

The present invention relates to a method for inspecting a line width of a pattern on an object to be inspected with different types of patterns rendered thereon, said method comprising: A method for inspecting a line width of a pattern on an object to be inspected with different types of patterns rendered thereon, comprising: imaging the object to be inspected and obtaining an optical image; creating a reference image from design pattern data; preparing an inspection recipe comprising one or more templates and parameter settings necessary for the inspection; checking the pattern and the template against each other, and selecting the reference image which corresponds to the template; detecting a first edge and a second edge in the selected reference image in accordance with the parameter settings using a standard coordinate; detecting a first edge of the optical image corresponding to the first edge of the selected reference image and a second edge of the optical image corresponding to the second edge of the selected reference image; and determining an inspection value by acquiring the difference between the line width of the optical image and the reference image using the first edge and second edges of the optical image and the first and second edges of the reference image.

In another embodiment of the present invention, a method for inspecting an amount of positional aberration of a pattern on an object to be inspected with different types of patterns rendered thereon, said method comprising: imaging the object to be inspected and obtaining an optical image; creating an reference image from design pattern data; preparing an inspection recipe comprising one or more templates and a parameter settings necessary for the inspection; checking the pattern and the template against each other, and selecting the reference image which corresponds to the template; detecting a first edge and a second edge in the selected reference image in accordance with the parameter settings using a standard coordinate; detecting a first edge of the optical image corresponding to the first edge of the selected reference image and a second edge of the optical image corresponding to the second edge of the selected reference image; and determining an inspection value by acquiring the amount of positional aberration between the optical image and the reference image by using the first and second edges of the optical image, and the first and second edges of the reference image.

In another embodiment of the present invention, a method for inspecting a line width of a pattern on an object to be inspected with different types of patterns rendered thereon, said method comprising: imaging the object to be inspected and obtaining an optical image; preparing an inspection recipe comprising one or more templates and a parameter setting necessary for the inspection; checking the pattern and the template against each other, and selecting the optical image which corresponds to the template; detecting a first edge and a second edge in the selected optical image in accordance with the parameter settings using a standard coordinate; determining an inspection value by measuring the line width between the first edge and the second edge.

In another embodiment of the present invention, a method for inspecting a line width of a pattern on an object to be inspected with different types of patterns rendered thereon, said method comprising: imaging the object to be inspected and obtaining an optical image; creating a reference image from design pattern data; measuring a line width of the pattern in the reference image; registering an obtained measurement value; registering the range of the obtained measurement values, and the range of threshold values centering on the measurement value; determining whether a pattern having a line width that matches the registered values exists in the optical image, and if such a pattern exists, measuring the line width of this pattern.

In another embodiment of the present invention, a method for inspecting a line width of a pattern on an object to be inspected with different types of patterns rendered thereon, said method comprising: imaging the object to be inspected and obtaining an optical image; registering a calculated value, and the range of threshold values centering on the calculated value; determining whether a pattern having a line width that matches the registered values exists in the optical image, and if such a pattern exists, measuring the line width of this pattern.

In another embodiment of the present invention, an inspection system which illuminates light on to an object to be inspected, receiving an image of the object to be inspected in an image sensor, and inspecting a pattern rendered on the object to be inspected, said system comprising: an image sensor; an optical image acquisition part for acquiring the image from the image sensor; a creating part to create reference image from design pattern data; a selecting part to select the reference image which corresponds to the template, said part utilizing an inspection recipe comprising one or more templates and a parameter setting necessary for the inspection; a detecting part to detect a first edge and a second edge in the selected reference image in accordance with the parameter setting using a standard coordinate; a detecting part to detect a first edge of the optical image corresponding to the first edge of the selected reference image, and a second edge of the optical image corresponding to the second edge of the selected reference image; and an acquisition part for acquiring an inspection value by measuring a line width difference of the optical image and the reference image using the first edge and second edges of the optical image and the first and second edges of the reference image.

In a final embodiment of the present invention, an inspection system which illuminates light on to an object to be inspected, receiving an image of the object to be inspected in an image sensor, and inspecting a pattern rendered on the object to be inspected, said system comprising: an image sensor; an optical image acquisition part for acquiring the image from the image sensor; a creating part to create reference image from design pattern data; a selecting part to select the reference image which corresponds to the template, said part utilizing an inspection recipe comprising one or more templates and a parameter setting necessary for the inspection; a detecting part to detect a first edge and a second edge in the selected reference image in accordance with the parameter setting using a standard coordinate; a detecting part to detect a first edge of the optical image corresponding to the first edge of the selected reference image, and a second edge of the optical image corresponding to the second edge of the selected reference image; an acquisition part for acquiring an inspection value by measuring an amount of positional aberration of the optical image and the reference image using the first edge and second edges of the optical image and the first and second edges of the reference image.

BRIEF DESCRIPTION OF THE DRAWINGS

FIG. 6 is one example of a display screen showing parameter settings.

DETAILED DESCRIPTION OF THE EMBODIMENTS

Figure 1:
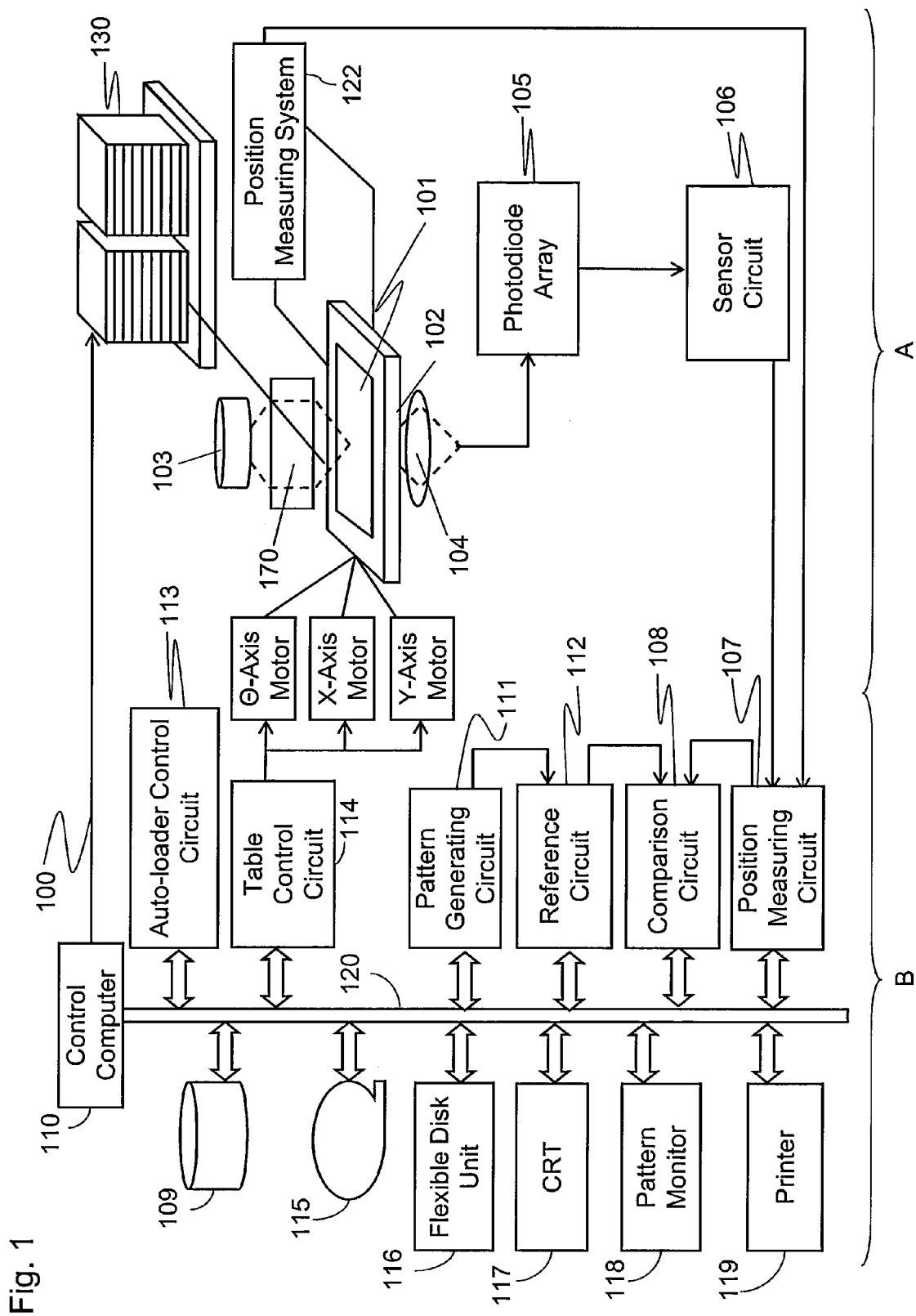
FIG. 1 is a diagram showing the configuration of an inspection system according to the present embodiment.

FIG. 1 is a constitutional view of an inspection system in the present embodiment. In the present embodiment, the object to be inspected is a mask used for photolithography or the like. The inspection system in the present embodiment is a Die to Database inspection system, and the reference image is created from design pattern data formed on a mask.

As shown in FIG. 1, an inspection system 100 has an optical image acquisition part A and a control part B.

The optical image acquisition part A includes a light source 103, an XYθ table 102 capable of moving in a horizontal direction (X direction, Y direction) and a rotation direction (θ direction), an illumination optical system 170 which constitutes a transmission illumination system, a magnifying optical system 104, a photodiode array 105, a sensor circuit 106, a position measurement system 122, and auto-loader 130.

In the control part B, a control computer that is responsible for the control of the entire inspection system 100 is connected via a bus 120 which is a data transmission channel to a position measuring circuit 107, a comparison circuit 108, a reference circuit 112, a pattern generating circuit 111, an auto-loader control circuit 113, a table control circuit 114, a magnetic disk device 109 (which is one example of a storage device), a magnetic tape device 115, a flexible disk unit 116, a CRT 117, a pattern monitor 118, and a printer 119. The XYθ table 102 is driven by an X-axis motor, a Y-axis motor, and an θ-axis motor which are controlled by the table control circuit 114. A step motor, for example, can be used for these motors.

The design pattern data, which is basis data of a database system is stored in the magnetic disk device 109, and it is read out in accordance with the progression of the inspection and then sent to the pattern generating circuit 111. In the pattern generating circuit 111, the design pattern data is converted into image data (bit pattern data). Subsequently, the image data is sent to the reference circuit 112, and then used in the generation of a reference image, which then becomes a basis image.

FIG. 1 illustrates the constitutional components necessary for the present embodiment, but other known components may be used.

Figure 2:
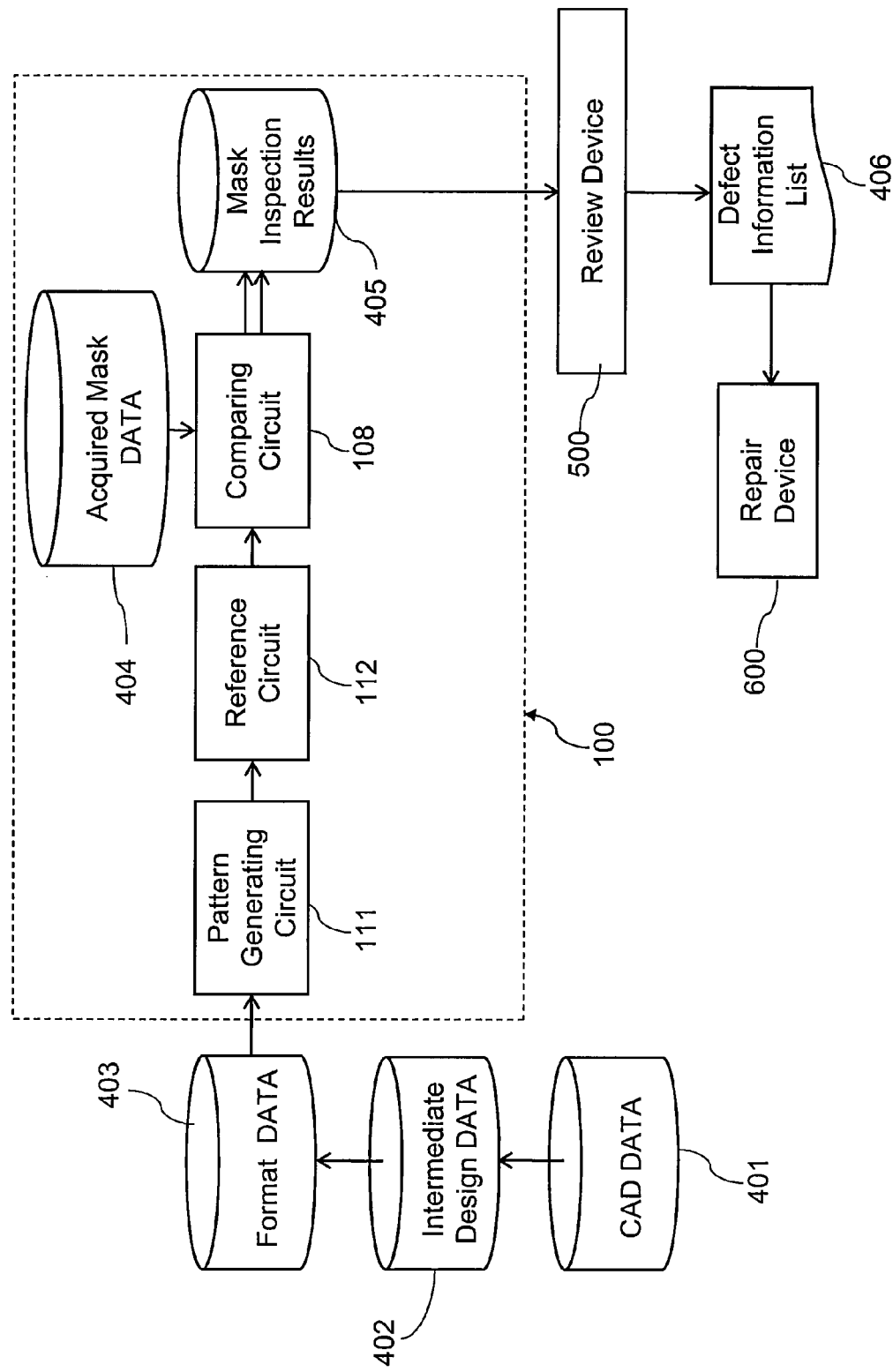
FIG. 2 is a schematic diagram showing a flow of data according to the present embodiment.

FIG. 2 is a schematic diagram showing the flow of data in the present embodiment.

As shown in FIG. 2, CAD data 401 created by a designer (user) is converted to intermediate design data 402 in a hierarchical format such as OASIS. Design pattern data that is created for each layer and formed on each mask is stored in as intermediate design data 402. In general, the inspection system 100 is not configured to be able to directly read the OASIS data. Format data unique to each manufacturer of the inspection system 100 is used. Therefore, the OASIS data is converted into format data 403 unique to each inspection system for each layer and then input into the inspection system 100. The format data 403 can be made into data unique to the inspection system 100, but it can also be made into data compatible with a lithography system.

The format data 403 is input into the magnetic disk device 109 of FIG. 1. In other words, the design pattern data used during formation of a pattern of a photomask 101 is stored in the magnetic disk device 109.

The design pattern data includes pattern features each consisting of basic shapes such as rectangles and triangles. For example, figure data which is information of coordinates (x, y) at a reference position of the figures, length of the sides, and figure codes, which are identifiers that distinguish the figure type such as rectangle, triangle, wherein the figure data defines the shape, size, position, and the like of each pattern figure, is stored in the magnetic disk device 109.

Furthermore, an assembly of figures, which exist in a range of approximately several-tens μm is generally called a cluster or a cell, and data is organized using such clusters or cells. In a cluster or cell, arrangement coordinates, or the description of figures are also defined for cases in which various figures are arranged individually or arranged repeatedly at a certain interval. Cluster or cell data is further arranged in strip-shaped regions whose width is several hundred μm and whose length is approximately 100 nm, which corresponds to the entire length in the X direction or Y direction of the photomask, and these regions are called frames or stripes.

The design pattern data is read by the pattern generating circuit 111 via the control computer 110 from the magnetic disk device 109.

The pattern generating circuit 111 generates data of each pattern feature, and interprets the shape code in the data indicative of the shape of the pattern feature and obtains its dimensions. The pattern generating circuit 111 then divides the pattern into a virtual grid of squares (or grid elements) having calculated quantization dimensions, and produces 2-bit or other multiple-bit design image data of the design pattern segment in each grid element. By using the produced design image data, the pattern generating circuit 111 calculates the design pattern occupancy in each grid element (corresponding to a sensor pixel). This pattern occupancy in each pixel represents the pixel value.

Next, the design pattern data converted to two-valued or multi-valued image data (design image data) as described above is sent to the reference circuit 112. In the reference circuit 112, the design image data, which is image data of the figures sent to the reference circuit 112, is subjected to appropriate filter processing.

Figure 3:
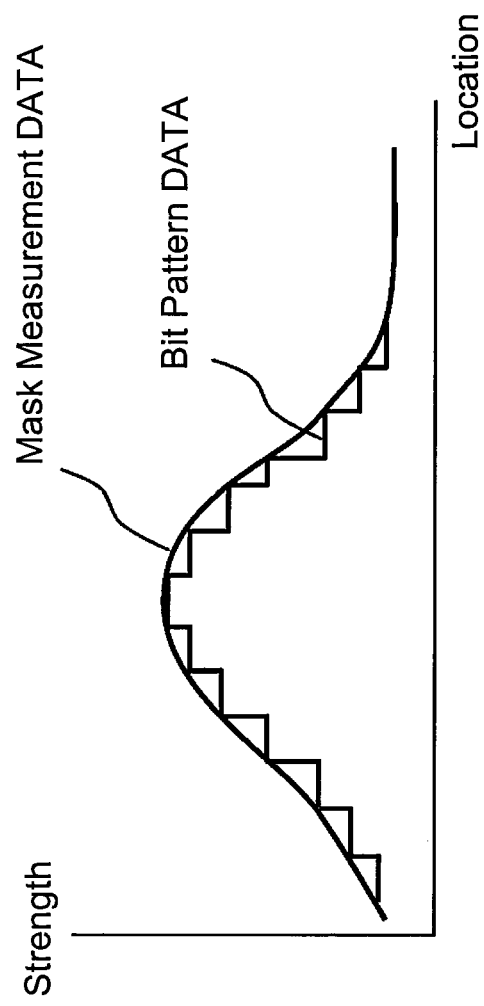
FIG. 3 is a diagram illustrating the filtering according to the present embodiment.

FIG. 3 explains the filtering process.

Acquired mask measurement data 404, which is an optical image obtained from the sensor circuit 106, is somewhat "blurred" due to resolution characteristics of the optical system and due to the aperture effect of the photodiode array, that is, this optical image is a spatially low-pass filtered image. Therefore, by subjecting bit pattern data (which is converted design pattern data in which the image intensity (gray value) has become a digital value) to filter processing, it can be conformed to match the "blurred" acquired mask measurement data 404. In this way, a reference image is created which can be compared to the acquired mask measurement data 404.

Next, a method for acquiring the mask measurement data 404 will be explained using FIGS. 1 and 4.

In FIG. 1, an optical image of the photomask 101, i.e. the mask measurement data 404, is acquired by the optical image acquisition part A. The acquired mask measurement data 404 is an image of a mask on which a figure based on the figure data included in the design pattern is rendered. A specific method for acquiring the mask measurement data 404 is as follows.

The photomask 101, which is the object to be inspected, is mounted upon the XYθ table 102 movable in two horizontal directions by X- and Y-axis motors and rotatable in a horizontal plane by a θ-axis motor. Next, light is irradiated from the light source 103 disposed above the XYθ table 102 onto the pattern formed on the photomask 101. In more detail, a light beam irradiated from the light source 103 is irradiated on the photomask 101 via the illumination optical system 170. The magnifying optical system 104, the photodiode array 105, and the sensor circuit 106 are disposed below the photomask 101. Light which passes through the photomask 101 is imaged as an optical image on the photodiode array 105 via the magnifying optical system 104. Herein, the magnifying optical system 104 can also be configured so that automatic focus adjustment is carried out by an automatic focusing mechanism (not illustrated). Furthermore, although not illustrated, the inspection system 100 can also be configured so that light is irradiated from below the photomask 101, reflected light is irradiated to a second photodiode array via a magnifying optical system, and transmitted light and reflected light are collected simultaneously.

Figure 4:
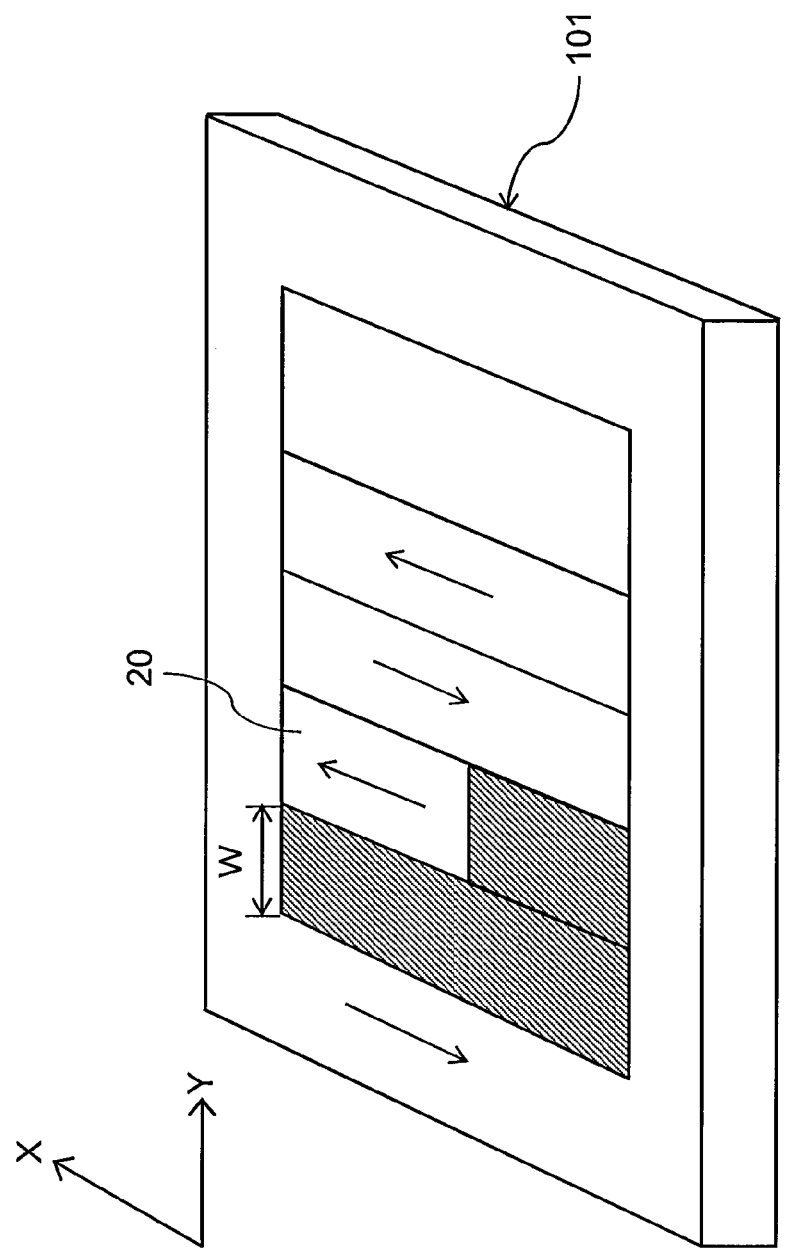
FIG. 4 is a diagram illustrating the way in which the mask measurement data is acquired according to the present embodiment.

FIG. 4 explains a procedure for acquiring the mask measurement data 404.

As shown in FIG. 4, the inspection region is virtually divided in the Y direction into a plurality of strip-shaped inspection stripes 20 having a scan width W. The operation of the XYθ table 102 is controlled so that the divided inspection stripes 20 are continuously scanned, and an optical image is acquired while the XYθ table 102 is moving in the X direction. An image having a scan width W as shown in FIG. 4 is continuously acquired via the photodiode array 105. When an image in a first inspection stripe 20 is acquired, an image having a scan width W in a second inspection stripe 20 is similarly continuously acquired while the XYθ table 102 is moving in the opposite direction. An image in a third inspection stripe 20 is acquired while the XYθ table 102 moves in the opposite direction to the direction in which the image in the second inspection stripe 20 was acquired, i.e. in the same direction in which the image in the first inspection stripe 20 was acquired. In this way, an image is continuously acquired, thereby reducing processing time.

The image of the pattern imaged on the photodiode array 105 is subjected to opto-electric conversion, and then further subjected to A/D (analog digital) conversion in the sensor circuit 106. An image sensor is provided in the photodiode array 105. As an example of an image sensor, mention may be made of a TDI (Time Delay Integration) sensor. For example, the pattern of the photomask 101 is imaged by the TDI sensor while the XYθ table 102 is continuously moving in the X-axis direction.

The XYθ table 102 is driven by the table control circuit 114 under the control of the control computer 110, and is capable of moving by a system such as 3 axis (X-Y-θ) motors, which drive in the X direction, the Y direction, and the θ direction. Step motors, for example, can be used for the X-axis motor, the Y-axis motor, and the θ-axis motor. The movement position of the XYθ table 102 is measured by the position measurement system 122 and sent to the position measuring circuit 107. For the position measurement system 122, for example, a measurement system using a laser is used. Further, the photomask 101 on the XYθ table 102 is configured to be automatically conveyed from the auto-loader 130 driven by the auto-loader control circuit 113 and then automatically discharged after completion of the inspection.

The acquired mask measurement data 404 output from the sensor circuit 106 is sent to the comparison circuit 108 together with data showing the position of the photomask 101 on the XYθ table 102 output from the position measuring circuit 107. The acquired mask measurement data 404 is, for example, 8-bit unsigned data, and expresses the gradation of the brightness of each pixel. Further, the reference image described above is also sent to the comparison circuit 108.

In the comparison circuit 108, the acquired mask measurement data 404 sent from the sensor circuit 106 and the reference image generated in the reference circuit 112 are compared using an appropriate comparison determination algorithm. The comparison is conducted with an algorithm of a transmission image only, and algorithm of a reflection image only, or an algorithm combining transmission and reflection. Further, a plurality of algorithms can be selected in accordance with the nature of the defects. A threshold value is set for each algorithm, and a result having a reaction value exceeding the threshold value is detected as a defect. In this case, first, an interim threshold value is set for the algorithm, and the result of defect inspection carried out based on this threshold value is reviewed in a review step to be explained below. This process is repeated, and when it is determined that a sufficient defect detection range has been obtained, the above-described interim threshold value is determined to be the threshold value of the algorithm.

As a result of the comparison, if the difference between the acquired mask measurement data 404 and the reference image exceeds the threshold value, that position is determined to be a defect. If determined to be a defect, the coordinates thereof and the acquired mask measurement data 404 and the reference image, which are the basis of the defect determination, are stored in the magnetic disk device 109 as a mask inspection result 405.

The mask inspection result 405 is sent to a review device 500, which is an external device of the inspection system 100. The review is an operation performed by an operator to determine whether a detected defect will become a problem. In the review device 500, an image of the defect positions of the mask is displayed while moving the table on which the mask is mounted so that the defect coordinates of each defect can be observed. At the same time, the conditions for determining a defect determination and the optical image and reference image, which are the basis for the determination, are displayed side by side on a screen so that they can be confirmed. By displaying the defects on the mask and the conditions of the wafer transfer image side by side in the review step, it becomes easy to determine whether the mask pattern should be corrected. In general, since the projection from the mask to the wafer is reduced in size by approximately ¼, this reduced scale is taken into consideration when displaying side by side.

All of the defects detected by the inspection system 100 are differentiated in the review device 500. The differentiated defect information is returned to the inspection system 100 and stored in the magnetic disk device 109. If even one defect requiring correction is confirmed in the review device 500, the mask is sent together with a defect information list 406 to a correction device 600, which is an external device of the inspection system 100. For pattern defects, the method of correction differs depending on whether the defect type is a convex defect or a concave defect. Therefore, the type of defect, including differentiation of concave/convex defects and the coordinates of the defect are included in the defect information list 406. For example, a differentiation between required trimming or supplementing of the light-shielding film, and pattern data for identifying the pattern locations, which should be corrected by the correction device, are included.

The inspection system 100 may have its own a review function. In this case, the mask inspection result 405 is displayed together with extra information of the defect determination on a CRT 117 of the inspection system 100 or on the screen of a separately configured computer.

In the review step, the defects are displayed on a monitor based on the data created from the inspection result, and the operator determines whether these defects will actually become a problematic and classifies the defects accordingly. More specifically, a comparison image is generated from the optical image and the reference image, and the defects, displayed in the comparison image, are reviewed by the operator. The pixel data in these images is expressed with a gradation value for each pixel. In other words, one value is given from 0 gradation to 255 gradation from a color palette having gradations values of 256 stages, and a rendered pattern and defects are displayed according to this value.

The optical image is obtained upon imaging a pattern that was actually rendered, and a cross-section of the pattern edge does not normally have an ideal shape as specified in the rendering data. For example, even if the cross-section shape of the pattern is a rectangle in the rendering data, the cross-section shape often has a gently tapered shape in the actual pattern. Therefore, the gradation value gradually changes in the vicinity of the pattern edge. Thus, during the defect determination process, it is necessary to specify where the pattern edge is. Therein, in the case of a line pattern, a location at which the gradation value fluctuates largely is considered to be a pattern edge, and the distance between the pattern edges at both ends of the line, i.e. the line width, is measured. The line width of the obtained optical image is compared to the line width obtained from the reference image, and the difference between them is defined as the line width difference ($\Delta$CD). Further, the optical image and the reference image are also compared with regard to a difference in the position of the pattern edges, and the difference between these positions is defined as the amount of positional aberration.

As explained above, when the line width of a pattern or the line width difference and amount of positional aberration between patterns is measured, a problem can arise in that there are fluctuations in the measurement value depending on the shape and size of the patterns. It is presumed that the reason for this is that original errors between the reference image and the optical image, which are generated during production of the reference image, are different depending on the pattern. In other words, the reference image is an image resembling the optical image obtained upon subjecting the design pattern data to mathematical processing, but there are naturally some deviations between the image generated and the actual optical image. These deviations differ depending on the pattern. Therefore, when the line width of a pattern or the line width difference and amount of positional aberration between patterns is uniformly measured across the entire surface of the mask for the optical image and the reference image, the natural deviations between the reference image and the optical image for each pattern are reflected in the measurement values, and thus the measurement values become dependent on the pattern. Therefore, an accurate distribution across the entire surface of the mask, i.e. an accurate distribution of line width or line width difference, or distribution of positional aberration cannot be found. This problem is particularly prominent in a logic mask with many patterns thereon.

In the present embodiment, only a specific pattern is extracted, and the line width of the pattern or the line width difference and amount of positional aberration between patterns in the optical image and the reference image therein are measured. In this way, the mixing of measurement values, which differ depending on the pattern, can be prevented, and a relative measurement accuracy can be guaranteed. As a method for extracting a specific pattern, mention may be made of 1) pattern matching of images, and 2) specifying the line width.

First, a method in which a specific pattern is extracted by pattern matching of the images, and then the measurement of line width of the pattern or the line width difference and amount of positional aberration between patterns in the optical image and the reference image for each extracted pattern will be explained.

Figure 5:
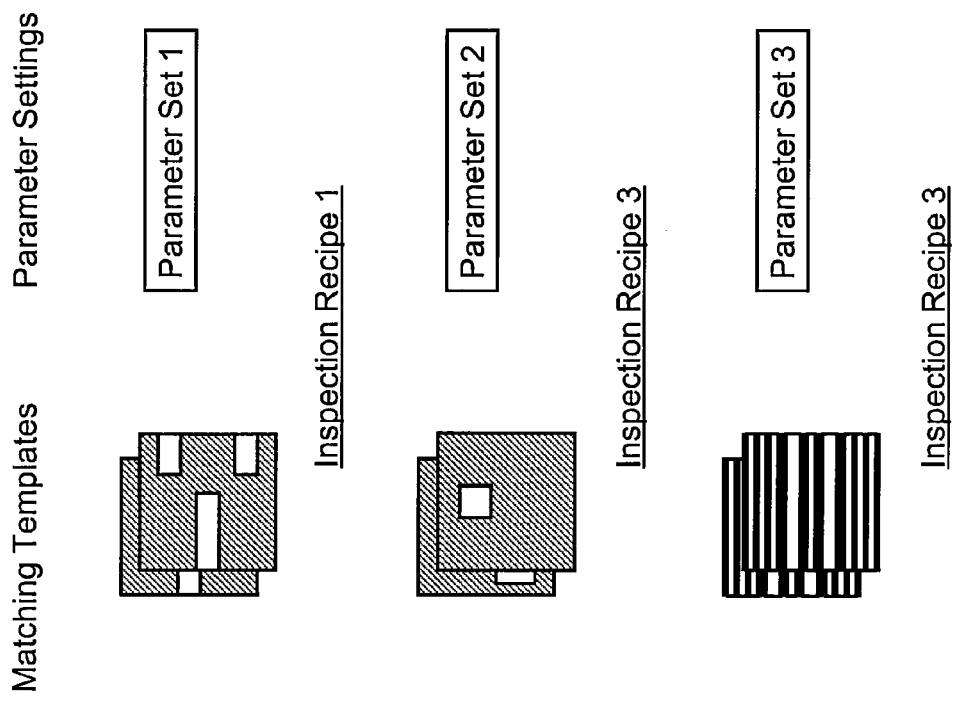
FIG. 5 is a diagram showing each inspection recipe having one or more registered templates and parameter settings.

In this method, pluralities of inspection recipes are prepared. An "inspection recipe" can be explained as a combination of templates and parameter settings. As shown in FIG. 5, each inspection recipe has one or more registered templates and parameter settings, and these are stored in the magnetic disk device 109 of FIG. 1, for example. The parameter setting has a first edge search setting, a second edge search setting, and other settings. The first edge and the second edge are pattern edges serving as reference edges when measuring the line width of the pattern or the line width difference between patterns in the optical image and the reference image.

As the first edge search setting and the second edge search setting, mention may be made of a mask ID showing information about the mask, a template designation, initial search coordinates and final search coordinates which are coordinates that serve as measurement points, a width to be measured, a threshold value setting for the measurement value, a black-white designation of the screen, a method for specifying the final coordinates, and the like. Further, as the other settings, mention may be made of a control value of CD (Critical Dimension), a control value of positional aberration, and the like. A control value is the difference between a set value and an actual value in the pattern. FIG. 6 is one example of a display screen showing parameter settings.

The other settings mentioned above also include a designation of the target of measurement regarding whether to measure the difference between the optical image and the reference image or measure the dimensions of the optical image. In other words, the target subjected to pattern matching with the registered templates may be either the reference image or the optical image. In the case that matching with the optical image is carried out, there is an advantage in that it is not necessary to create a reference image. However, since matching is carried out such that the pattern is positioned at the center of the image, the positional aberration cannot be understood. Therefore, matching with the optical image is designated for the purpose of measuring only the line width.

The consecutive steps of extracting a specific pattern by pattern matching of the images and then measuring the line width of the pattern or the line width difference and amount of positional aberration between patterns in the optical image and the reference image for each extracted pattern is carried out in the comparison circuit 108 of FIG. 1.

The optical image output from the sensor circuit 106 in FIG. 1 is sent to the comparison circuit 108 together with data showing the position of the mask on the XY$\theta$ table 102 output from the position measuring circuit 107. The design pattern data subjected to filter processing in the reference circuit 112 becomes the reference image and is sent to the comparison circuit 108. In the comparison circuit 108, the optical image sent from the sensor circuit 106 and the reference image generated in the reference circuit 112 are compared.

In the present embodiment, in the comparison circuit 108, a pattern and a template are checked against each other, and then a reference image corresponding to the template is determined. Next, coordinates (normally the center coordinates) in the reference image that is determined are set as standard coordinates, and a first edge and a second edge are determined in accordance with the settings defined in the parameter setting. Specifically, edge points are detected with sub-pixels using a calculated threshold value with respect to a profile of pixel values in the width direction of the design pattern in which the edge direction has been identified. For example, in the reference image, if a position at which the pixel value changes between "200" and "0" is considered to be an edge point, this edge point is detected using the threshold value. At this time, the threshold value includes a case in which it matches the brightness of a specific pixel and a case in which it falls between the brightness of two pixels.

After the first edge and the second edge are determined, a measurement of the dimension in the width direction of the design pattern, i.e. a measurement of the line width, and a detection of the edge position is carried out based on the detected edge points in accordance with the settings defined in the parameter setting.

The comparison circuit 108 reads the optical image, detects an edge corresponding to the first edge and an edge corresponding to the second edge, calculates the line width difference or the amount of positional aberration between the optical image and the reference image, and then sets this as an inspection value.

In more detail, by measuring the difference between the optical image and the reference image, the line width difference or the amount of positional aberration between the patterns can be calculated.

Figure 13:
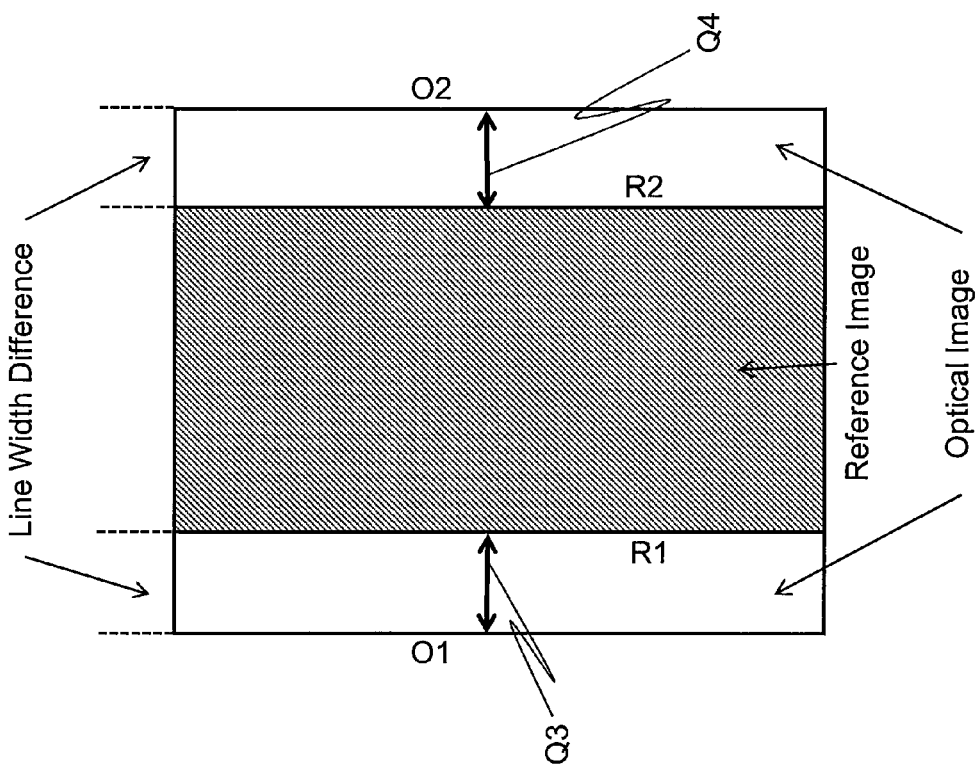
FIG. 13 is an image showing an example of a pattern having width measurement performed between the first optical image edge and the first reference image edge.

For example, a measurement of the dimension between the first edge of an optical image (O1) and the first edge of the reference image (R1) (as shown by Q3 in FIG. 13), and a measurement of the dimension between the second edge of the optical image (O2) and the second edge of the reference image (R2) (as shown by Q4 in FIG. 13) may be performed. Or the line width difference can be calculated by measuring the dimensions from the first edge O1 to the second edge O2 of the optical image (measurement Q1), and from the first edge R1 to the second edge R2 (measurement Q2) of the design pattern (which are the basis of the measurement of the dimension in the width direction and the edge position detection) as shown in FIG. 14, then calculating the line width difference from these two measurements.

Figure 14:
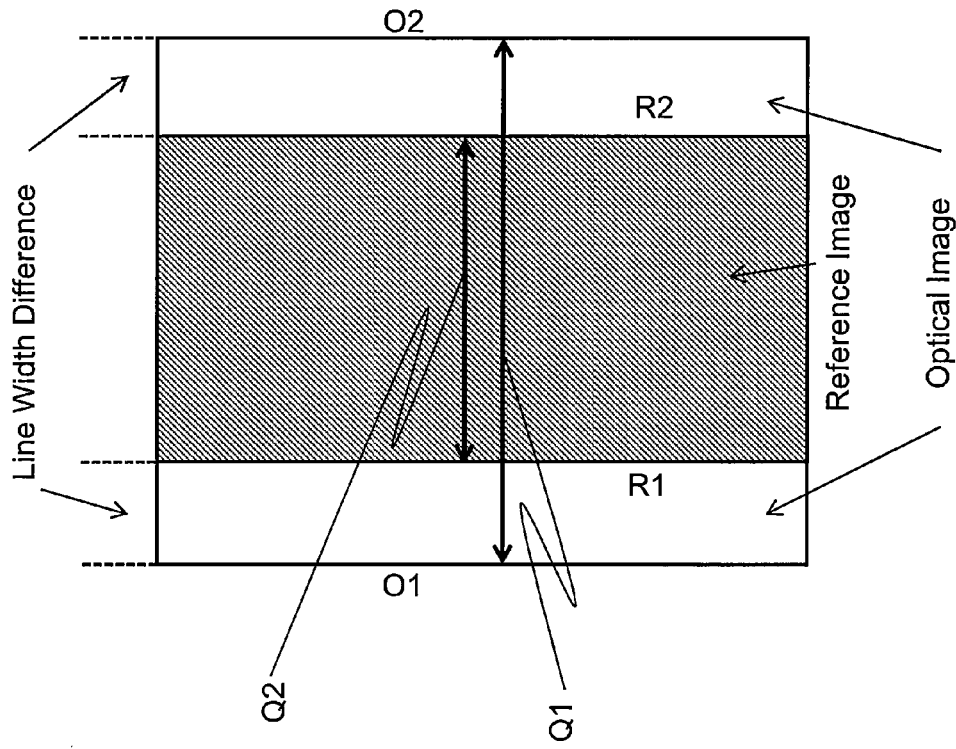
FIG. 14 is an image showing an example of a pattern having width measurement performed between the first and second optical image edge and the first and second reference image edge.

Alternatively, the amount of positional aberration can be calculated from one middle position of the first edge O1 and the second edge O2 of the optical image, and another middle position of the first edge R1 and the second edge R2 of the design pattern in FIG. 14, and by then comparing the difference between these positions.

The comparison circuit 108 determines whether the pattern formed on the mask is right or wrong based on the obtained inspection value. In more detail, it is determined that the pattern is outside of an allowable range when the line width difference or amount of positional aberration between patterns in the optical image and the reference image, which is the inspection value, exceeds the threshold value in the inspection recipe. In other words, when the inspection value is greater than the threshold value on the plus side or less than the threshold value on the minus side, it is determined that the pattern is defective.

The following is one example of the right/wrong determination with respect to the line width. This determination can also be carried out in the same way for the positional aberration.

First, an inspection stripe virtually positioned on the mask is divided horizontally and vertically into units with a fixed division width to form inspection regions. Therefore, a plurality of patterns exist in each inspection region.

Next, the line width in the X direction and Y direction is measured in a specific pattern extracted by pattern matching of the images.

Next, the results of the measurement of the line widths measured for each pixel are tallied and the line width difference are calculated, and then the rate of occurrence for each line width difference based on the obtained values are tallied. As the inspection value, an average value of the occurrences is calculated from the results of tallying the occurrences. If the occurrence distribution of the line width are graphed, in a normal part of the line width, the occurrence distribution of the line width difference are distributed centered on 0 nm, as in the design pattern data. In contrast, in an abnormal part of the line width, the occurrence distribution of the line width are distributed centered on a value that deviates from 0 nm.

Subsequently, it is determined whether the average value of the occurrence is within a calculated threshold value. If it is within the threshold value, it is considered acceptable, whereas if it exceeds the threshold value, it is considered unacceptable.

In the present embodiment, along with preparing a plurality of inspection recipes, a control value can be set for each inspection recipe, a ratio of the inspection result to the control value can be found and a degree of risk variance can be calculated, and then the degree of risk variance for each inspection recipe can be map-displayed. Alternatively, the plurality of inspection recipes can be superimposed to map-display the degree of risk variance. Herein, the degree of risk variance is an indicator expressing the deviance from the control value. For example, in the case that the CD control value is 15 nm and the CD inspection value is 5 nm, the degree of risk variance is expressed by the following formula:

$$(5/15) \times 100 = 33(\%)$$

The display of the specific control value can be determined by the operator. For example, a region with an average degree of risk variance in the measurement region may be displayed, or the region with the highest degree of risk variance may be displayed.

Figure 7:
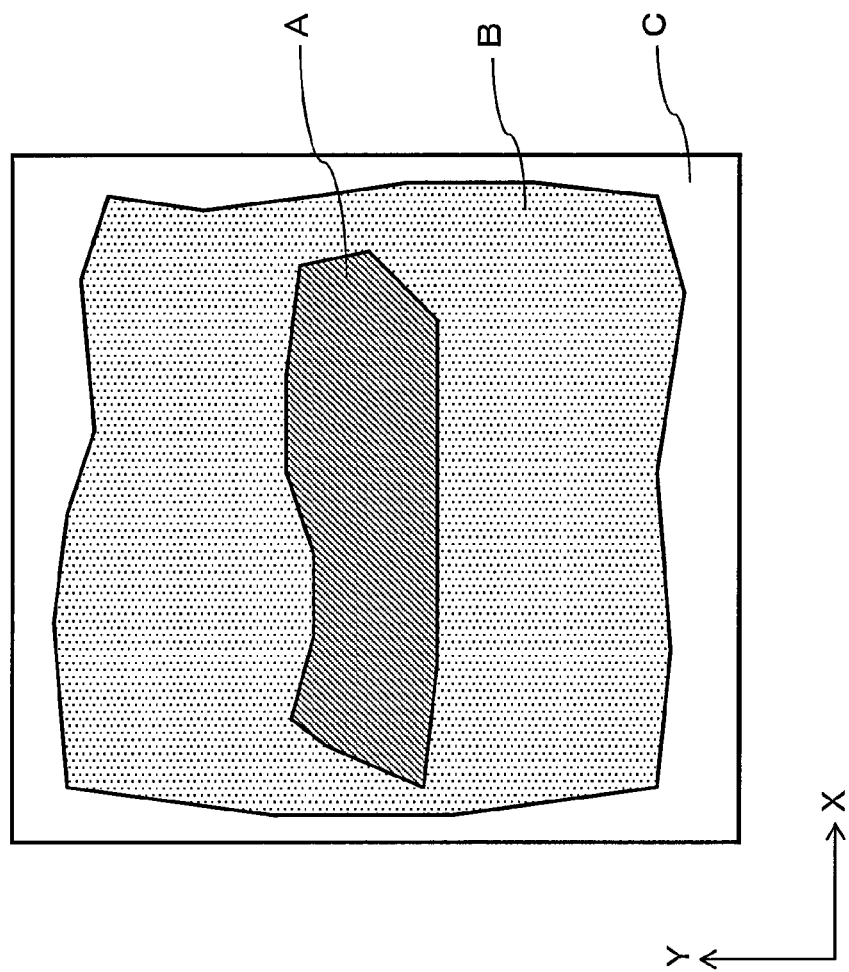
FIG. 7 is one example of a map display of the degree of risk variance.

FIG. 7 is one example of a map display of the degree of risk variance. In this example, the region is divided into each degree of risk variance and then displayed, and the degree of risk variance decreases in the order of A, B, and then C.

In a prior inspection method, in the edge parts at both ends in the width direction of the design pattern, an adjacent pair of pixels (edge pair) was searched to identify the edge direction of the design pattern.

Specifically, from a focus pixel, which is the center pixel in the design window, a search was carried out in four directions, consisting of the X direction, the Y direction, and the ±45° directions relative to the XY direction (8 directions if the + direction and − direction are considered). From the results thereof, a search direction in which a pair of pixels exists was detected, and it was recognized that the edge direction of the design pattern is in the direction orthogonal to the detected search direction. For example, if pixels corresponding to each edge point at both ends of the design pattern were detected by an X direction search, then these pixels were considered to be an edge pair, and the direction orthogonal to the X direction, which is the search direction, i.e. the Y direction, was recognized as the edge direction of the pattern. The edge points at both ends of the design pattern were detected with sub-pixels based on the pixel values of the detected edge pair, and then the dimension in the width direction of the design pattern was calculated from the edge points. The positional aberration of the edges was calculated by measuring the aberration of the overall pattern.

In this way, in the prior inspection method, the dimension in the width direction was found by searching for edge pairs and the aberration in the edge position was found from the aberration of the overall pattern, and there was no calculation of the coordinates of each edge. However, in this method, there is a problem in that the edge position changes depending on the shape of the pattern between the edges. For example, if a dimension α in the width direction of Pattern 1 shown in FIG. 8A is calculated, in the conventional method, a location which differs from the location originally intended for measurement may be measured.

Figure 8A:
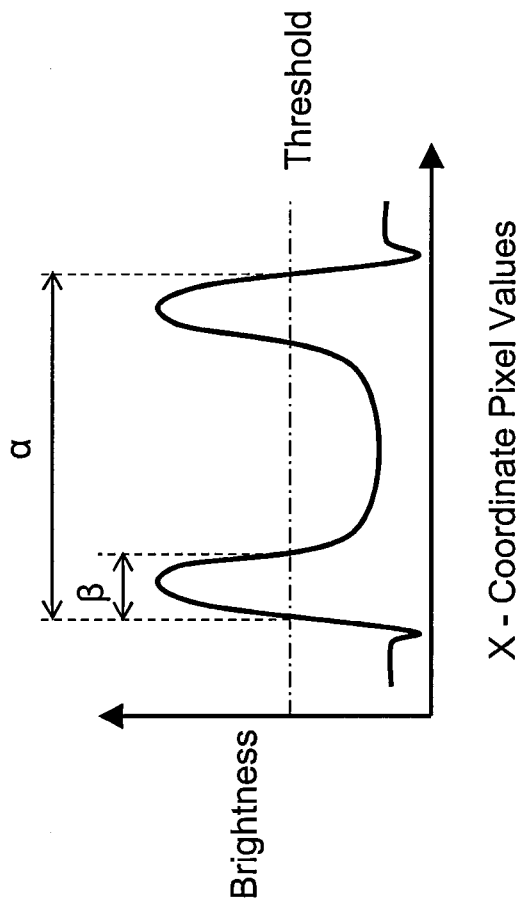
FIG. 8A is an example of a pattern to be scanned.
Figure 8B:
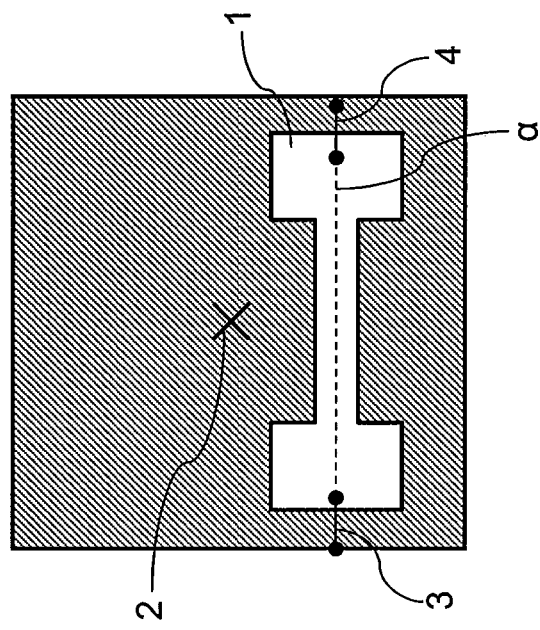
FIG. 8B shows the luminance changes in the scanning direction of the laser beam.

FIG. 8B shows the luminance changes in the scanning direction of the laser beam (the X direction) for Pattern 1 of FIG. 8A. In this case, the dimension originally intended for measurement is the length shown by reference symbol α, and the end parts of this dimension should be the edges. However, according to the conventional method, a problem arises in that it is determined that the edges are in the range shown by reference symbol β, and as a result, the part shown by reference symbol α cannot be measured.

In contrast, in the present embodiment, since matching reference coordinates are found and the coordinates of the edges are determined, measurement can be carried out without influence by the shape of the pattern between the edges. In other words, in FIG. 8A, matching reference coordinates 2 are established, and a first edge and a second edge are determined in accordance with the settings defined in the parameter setting. Specifically, edge points are detected with sub-pixels using a calculated threshold value with respect to a profile of pixel values in the width direction shown in FIG. 8B. Reference symbol 3 shows the search range for the first edge, and reference symbol 4 shows the search range for the second edge. By specifying the coordinates of the edges obtained as a result of the search, the part shown by reference symbol α in FIG. 8B can be measured regardless of the pattern between the edges. A measurement width can also be calculated and the average value within this measurement range can be used as the measurement value.

According to the method described above in which a specific pattern is extracted by pattern matching of the images and then the line width difference or amount of positional aberration between patterns in the optical image and the reference image for the extracted pattern is measured, by enabling a inspection recipe to be set between a plurality of masks, a dimension between patterns formed on a wafer can be measured bimposing the plurality of masks.

Figure 9C:
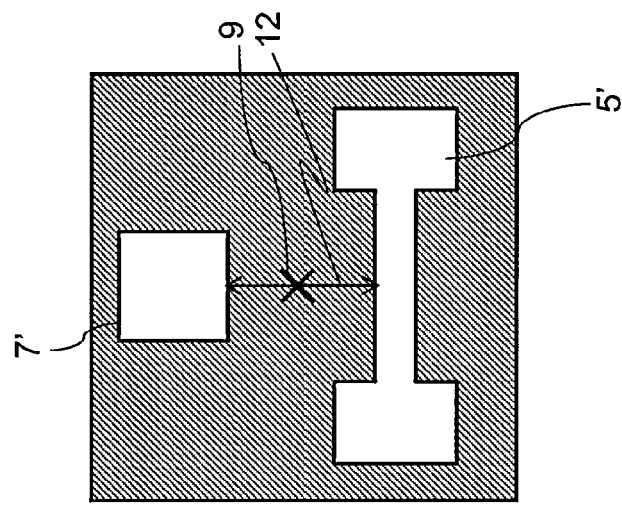
FIG. 9C is a pattern image transferred onto a wafer.
Figure 9B:
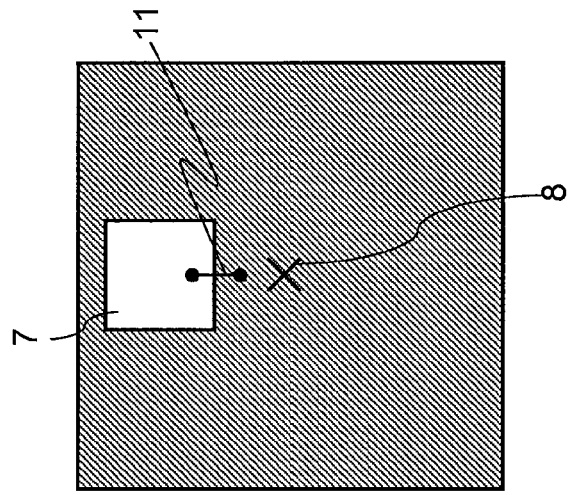
FIG. 9B is an image of a second mask.
Figure 9A:
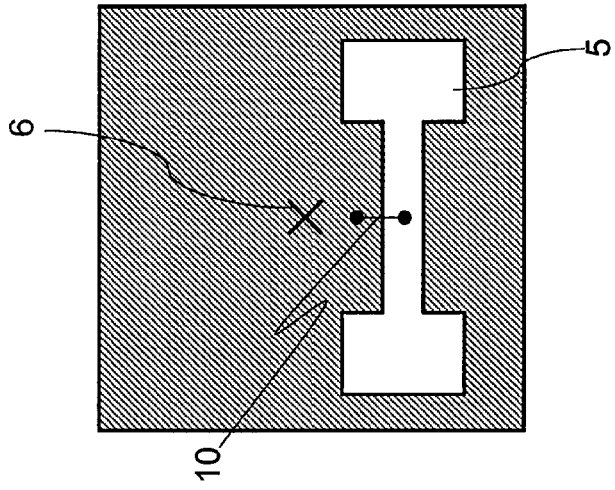
FIG. 9A is an image of a first mask.

FIG. 9A is an image of a first mask having a pattern 5, and FIG. 9B is an image of a second mask having a pattern 7. If the pattern 5 is transferred to a wafer using the first mask, and then the pattern 7 is transferred to the same wafer using the second mask, a pattern 5' and a pattern 7' are obtained as shown in FIG. 9C. In this case, if the first mask is specified with the first edge search setting and the second mask is specified with the second edge search setting, the dimension between the first edge and the second edge corresponds to the dimension between the pattern 5' and the pattern 7'. In FIGS. 9A to 9C, reference symbols 6, 8, and 9 are matching reference coordinates. Reference symbol 10 shows the first edge search range, and reference symbol 11 shows the second edge search range. Further, reference symbol 12 shows a desired measurement location, and this location is obtained by superimposing the first mask and the second mask.

Figure 10:
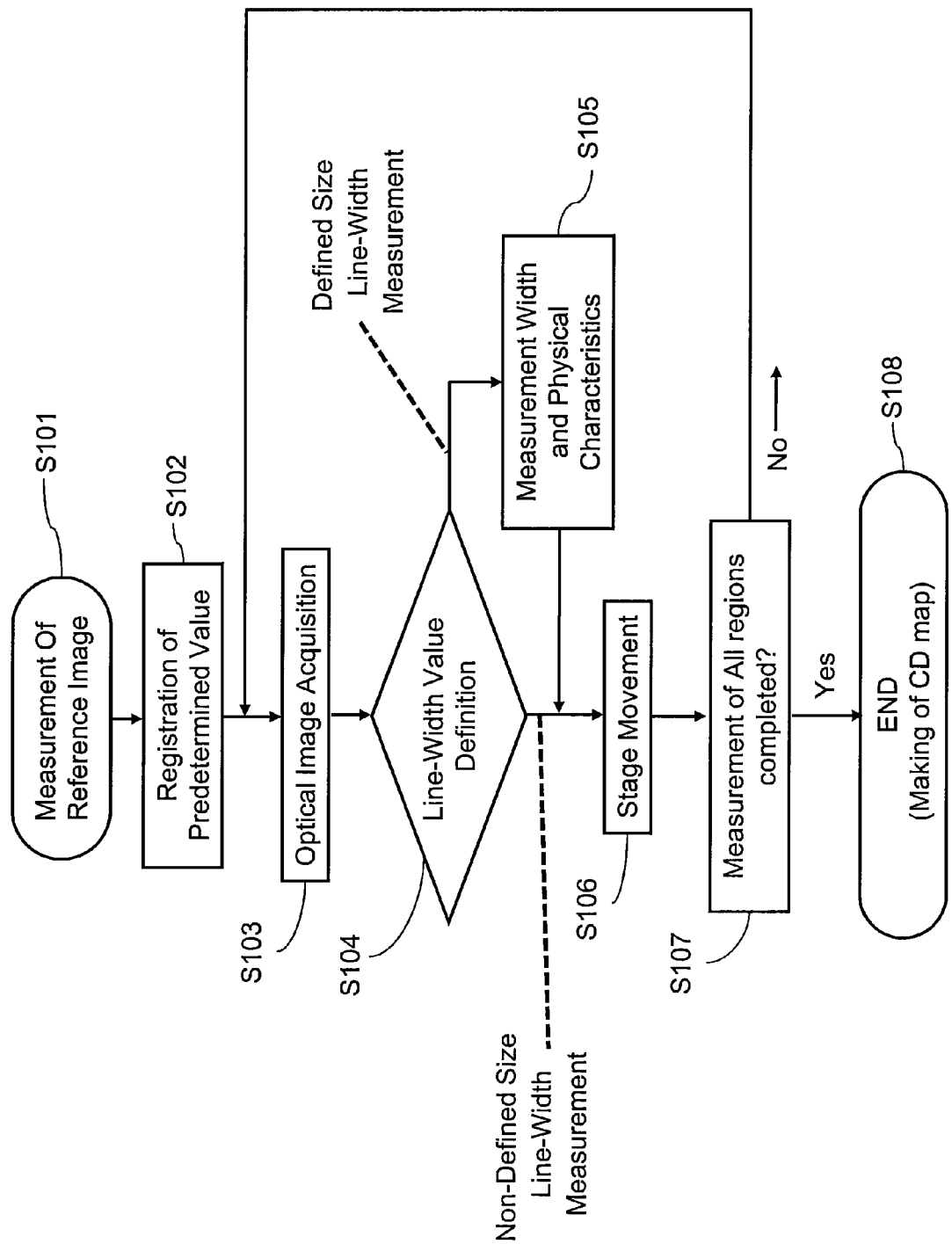
FIG. 10 is a flow chart showing the method of extracting a specific pattern by specifying the line width.

Next, a method in which a specific pattern is extracted by specifying the line width, and then the line width of the pattern or the line width difference between patterns in the optical image and the reference image for the extracted pattern will be explained. FIG. 10 is a flow chart showing this method.

As shown in FIG. 10, the line width of each pattern in the reference image is measured (S101), and values in a range of threshold values centered on the obtained measurement values are registered (S102). Instead of measuring, a calculated value may be designated, and this designated value as well as values in a calculated range centered on the designated value may be registered. Further, instead of the reference image, this method can be carried out on the optical image.

Next, the optical image is acquired (S103), and determination is performed during the line-width Value Definition step (S104), as to whether the optical image has a pattern having a line width matching the values registered in S102.

In S104, the line width is defined using a calculated allowable value.

Figure 11:
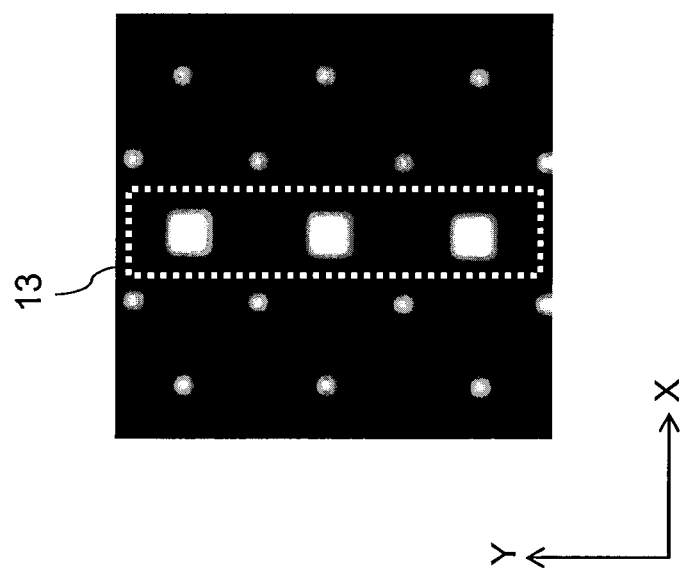
FIG. 11 is an image of the measurement target in the optical image as shown enclosed by the dotted line.

For example, in a case in which the registered line width in the X direction and Y direction is 300 nm±10 nm, the measurement target in the optical image of FIG. 11 is the pattern surrounded by a dotted line shown by reference symbol 13. The method proceeds to S105 in FIG. 10 and the line width measurement and the tallying of measurement values is carried out.

Meanwhile, the patterns other than the pattern surrounded by reference symbol 13 are not considered as measurement targets since they do not have the registered line width, and thus stage movement is performed (S106).

Even if the measurement is completed in S105, the method proceeds to S106 and stage movement is performed.

In S107, it is determined whether the measurement of the desired location has been completed across all regions of the mask. If the measurement has not been completed, the method returns to S103 and the same process is repeated.

However, if the measurement has been completed, the method proceeds to S108 and the successive steps are completed. A map of the line width error is then created using the obtained measurement result.

Figure 12:
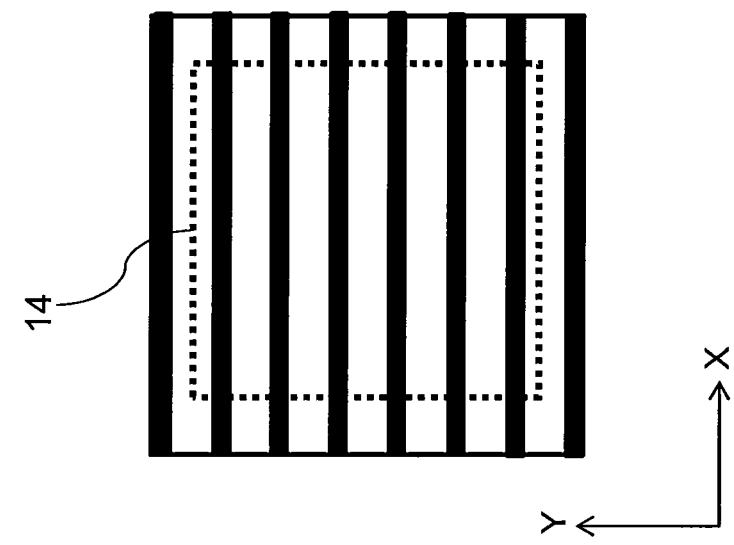
FIG. 12 is an image showing an example of a pattern surrounded by a dotted line to be read in the Y-direction.

In a case in which the registered line width is, for example, not designated in the X direction and designated as 100 nm±6 nm in the Y direction, as shown in FIG. 12, this corresponds to a line pattern which is long in the X-axis direction. In this case, in a pattern surrounded by a dotted line shown by reference symbol 14, the line width in the X-axis direction is not measured, and only the line width in the Y direction is measured.

As explained above, in the present embodiment, using a method performed by pattern matching of the images or a method performed by specifying the line width, only a specific pattern is extracted from a mask having a variety of patterns, and the line width of the pattern or the line width difference and amount of positional aberration between patterns in the optical image and the reference image for each extracted pattern is measured. Thereby, the mixing of measurement values, which differ depending on the pattern, can be prevented, and thus an accurate error distribution across the entire surface of the mask can be calculated. Further, since a map representing the distribution in the line width difference or a map representing the distribution of the amount of positional error can be created for each extracted pattern, the line width or positional error can be controlled for each pattern using the maps.

The features and advantages of the present invention may be summarized as follows:

According to the present invention, the distribution of the line width difference or the distribution of the amount of positional aberration of a pattern formed on an object to be inspected and a reference pattern can be accurately calculated.

It will be understood that the present invention is not limited to the embodiments described above since various alterations may be made thereto without departing from the spirit and scope of the invention.

The above description of the present embodiment has not specified apparatus constructions, control methods, etc. which are not essential to the description of the invention, since any suitable apparatus constructions, control methods, etc. can be employed to implement the invention. Further, the scope of this invention encompasses all pattern inspection systems and pattern inspection methods employing the elements of the invention and variations thereof, which can be designed by those skilled in the art.

Obviously many modifications and variations of the present invention are possible in the light of the above teachings. It is therefore to be understood that within the scope of the appended claims the invention may be practiced otherwise than as specifically described.

The invention claimed is:

1. A method for inspecting an amount of positional aberration of a pattern on an object to be inspected with different types of patterns rendered thereon, comprising:
   imaging the object to be inspected and obtaining optical images;
   creating reference images from design pattern data;
   preparing an inspection recipe comprising one or more templates used for pattern matching and parameter settings necessary for the inspection;
   selecting a pattern of a reference image which corresponds to a template selected from the inspection recipe;
   detecting a first edge and a second edge in the selected reference image in accordance with the parameter settings using a standard coordinate;
   selecting an optical image which corresponds to the selected reference image;
   determining an expected coordinate region within which to search for an edge of the selected pattern based on a matching reference coordinate in the parameter settings that identifies a same reference location in relation to the selected pattern in both of the selected reference image and the selected optical image;
   detecting a first edge in the selected optical image corresponding to the first edge in the selected reference image and a second edge in the selected optical image corresponding to the second edge in the selected reference image using the matching reference coordinate to search for at least one of the first edge and the second edge in the selected optical image only within the determined expected coordinate region; and
   determining an inspection value by acquiring an amount of positional aberration between the selected optical image and the selected reference image by using the first edge and the second edge of the selected optical image, and the first edge and the second edge of the selected reference image.

2. The method according to claim 1, comprising:
   acquiring the amount of positional aberration of the selected optical image and the selected reference image from the respective middle positions of the first edge and the second edge in the selected optical image and the respective middle position of the first edge and second edge in the selected reference image.

3. The method according to claim 1, comprising:
   determining a pattern corresponding to an inspection value which exceeds a threshold value in inspection recipe is defective.

4. The method according to claim 1, comprising:
   setting the inspection recipe between a plurality of objects to be inspected;
   detecting the first edge in the selected reference image and the first edge in the selected optical image corresponding to the first edge in the selected reference image in one object, and, the second edge in the selected reference image and the second edge in the selected optical image corresponding to the second edge in the selected reference image in another object.

5. An inspecting system which illuminates light on to an object to be inspected, receiving optical images of the object to be inspected in an image sensor, and inspecting a pattern rendered on the object to be inspected, said system comprising:
   a sensor circuit configured to acquire the optical images from the image sensor;
   a pattern generating circuit configured to generate design images data from design pattern data;
   a reference circuit configured to create reference images from the design images data; and
   a comparison circuit configured to select a pattern of a reference image which corresponds to a template by utilizing an inspection recipe comprising one or more templates used for pattern matching including the template and parameter settings necessary for the inspection, detect a first edge and a second edge in the selected reference image in accordance with the parameter settings using a standard coordinate, select an optical image corresponding to the selected reference image, determine an expected coordinate region within which to search for an edge of the selected pattern based on a matching reference coordinate in the parameter settings that identifies a same reference location in relation to the selected pattern in both of the selected reference image and the selected optical image, detect a first edge in the selected optical image corresponding to the first edge in the selected reference image and a second edge in the selected optical image corresponding to the second edge in the selected reference image using the matching reference coordinate to search for at least one of the first edge and the second edge in the selected optical image only within the determined expected coordinate region, and acquire an inspection value by measuring an amount of positional aberration between the selected optical image and the selected reference image by using the first edge and the second edge in the selected optical image and the first edge and the second edge in the selected reference image.

6. The inspecting system according to claim 5, wherein the comparison circuit is further configured to determine that a pattern corresponding to an inspection value which exceeds a threshold value in the inspection recipe is defective.

* * * * *